United States Patent [19]

Itoh

[11] Patent Number: 4,798,095
[45] Date of Patent: Jan. 17, 1989

[54] APPARATUS FOR DISTRIBUTING LIQUID SAMPLES AMONG TEST TUBES AND FOR DIVIDING THE TEST TUBES INTO GROUPS

[76] Inventor: Teruaki Itoh, 5-25, Kogaihonmachi, Kumamoto-shi, Kumamoto-ken, Japan

[21] Appl. No.: 39,952

[22] Filed: Apr. 20, 1987

[30] Foreign Application Priority Data

| Apr. 30, 1986 | [JP] | Japan | 61-66703[U] |
| Apr. 30, 1986 | [JP] | Japan | 61-66704[U] |
| Apr. 30, 1986 | [JP] | Japan | 61-66705[U] |
| Apr. 30, 1986 | [JP] | Japan | 61-66706[U] |
| Apr. 30, 1986 | [JP] | Japan | 61-66707[U] |

[51] Int. Cl.$^4$ .................. G01N 35/06; G01N 35/04
[52] U.S. Cl. ........................... 73/863.01; 422/63
[58] Field of Search ............ 73/864.91, 863.01; 422/63

[56] References Cited

U.S. PATENT DOCUMENTS 4,512,202  4/1985  Wright et al. ............... 73/864.91 X

FOREIGN PATENT DOCUMENTS

1381514  1/1975  United Kingdom.
1479210  7/1977  United Kingdom.
2116711  9/1983  United Kingdom.

Primary Examiner—Tom Noland
Attorney, Agent, or Firm—Nixon & Vanderhye

[57] ABSTRACT

A sample-transporting path is provided which includes holders for holding containers, either empty or filled with liquid samples, a conveyor for conveying the holders, and guide plates. The guide plates guide the holders holding filled containers to a first position where liquid samples will be sucked from some of the filled containers. Each of the holders has first and second annular grooves cut in the outer periphery. The guide plates are guide edges horizontally protruding from two parallel walls forming the path. These guide edges are inserted in the first annular groove of the holder. A stopper is provided at the first position. The stopper has a stopper pin which thrusts into the gap between the second annular grooves of any two adjacent holders, thereby stopping the holders located downstream of the path with respect to the stopper pin.

6 Claims, 7 Drawing Sheets

APPARATUS FOR DISTRIBUTING LIQUID SAMPLES AMONG TEST TUBES AND FOR DIVIDING THE TEST TUBES INTO GROUPS

BACKGROUND OF THE INVENTION

The present invention relates to an apparatus for distributing liquid such as a blood sample among a plurality of test tubes and for dividing the test tubes containing the small quantities of the liquid into groups, so that these groups will be transported to devices for analyzing the liquid for different items.

In order to analyze a blood sample for checking different items, it is necessary to distribute the sample, in small quantities, among a plurality of test tubes. When the blood sample is distributed by handwork, it is possibly contaminated. To eliminate or reduce this possibility of contamination, attempts have been made to provide an apparatus for automatically distributing a blood sample among a plurality of test tubes. Such an apparatus should meet various requirements. First, it must smoothly bring empty tubes to the position where the sample is distributed among these tubes. Secondly, it must distribute the sample among as many test tubes as possible within as short a time as possible. Thirdly, it must make it easy for the operator to identify the blood. Fourthly, it must easily and reliably divide the tubes containing small quantities of the sample into groups.

SUMMARY OF THE INVENTION

It is accordingly the object of the invention to provide an apparatus which can easily, reliably and fast distribute liquid among a plurality of test tubes and can easily, reliably and fast divide the test tubes containing the small quantities of the liquid into groups.

According to the invention, there is provided an apparatus comprising a sample-transporting path including holders for holding containers, a conveyor for conveying the holders, and guide means for guiding the holders to a first position where liquid samples will be sucked from some of the containers held by some of the holders; data-reading means for reading, from each of the container containing a liquid sample, data showing items for which the sample will be analyzed and data showing the identity of the sample; means for transporting the holders holding empty containers in the same number as the items of analysis to a second position where each liquid sample will be distributed among the empty containers; means for distributing the liquid sample in small quantities from each of the containers located in said first position, among the containers located in said second position, in accordance with the data read by the data-reading means; and means for dividing the containers containing the small quantities of the liquid samples into groups in accordance with the data read by the data-reading means. Each holder is a hollow cylinder having at least two annular grooves cut in its outer periphery. Said guide means has guide edges which can be inserted in the first annular groove of the holder.

DETAILED DESCRIPTION OF THE PREFERRED EMBODIMENT

Figure 1:
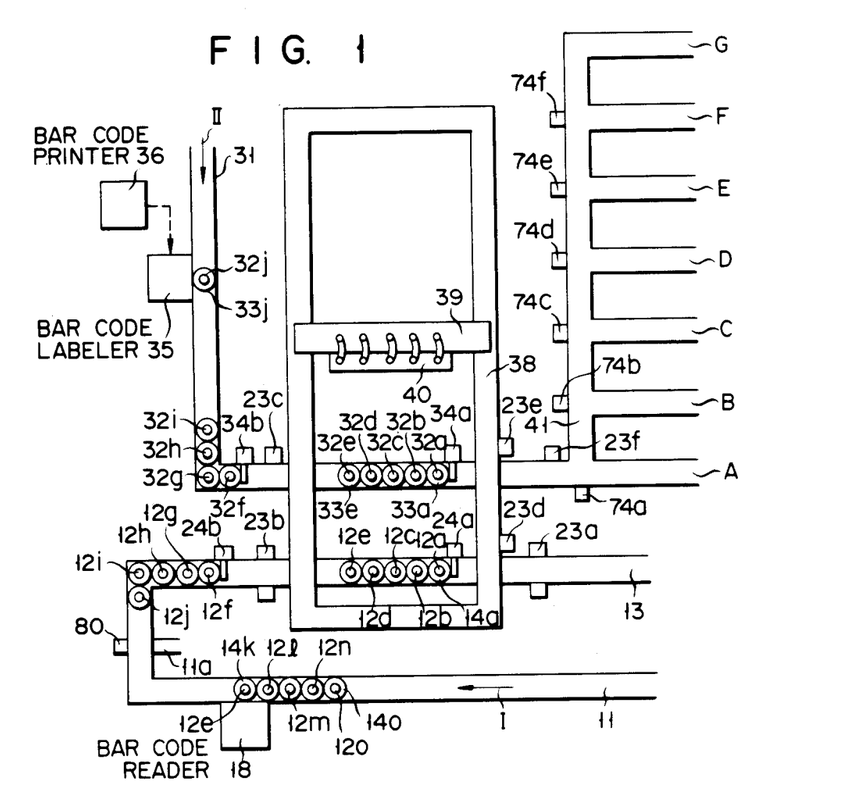
FIG. 1 is a front view schematically showing a liquid-distributing apparatus according to the present invention.
Figure 2:
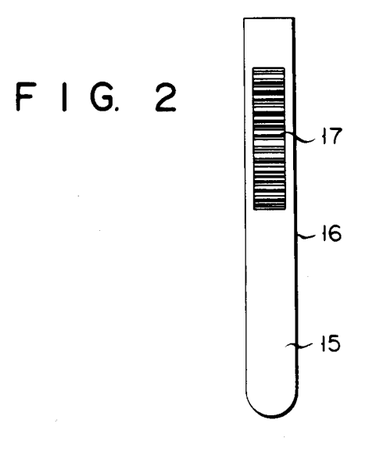
FIG. 2 shows a test tube containing a liquid sample, with a bar-code label put on its periphery.

One embodiment of the present invention, i.e., an apparatus for distributing a blood sample among test tubes, will now be described with reference to the accompanying drawings. As is shown in FIG. 1, tube holders 14a to 14o holding test tubes 12a to 12o containing blood samples are transported in path 11, one by one, toward outlet 13 in the direction of arrow I. FIG. 1 shows one of the test tubes, i.e., test tube 16 containing a predetermined amount of blood 15. A label is put on test tube 16. Printed on this label is a bar code 17 representing the identity of blood sample 15 and the items for which blood 15 will be analyzed.

Bar code 17 is read by bar code reader 18 provided beside path 11. The data by reader 18 is supplied to control device 19. Control device 19 comprises CPU 20 and main memory 21. The data is stored in main memory 21 under the control of CPU 20. Main memory 21 includes a ROM storing the program for controlling the apparatus, and a RAM for storing and providing various data items. The data output by bar code reader 18 is stored into this RAM.

Figure 3:
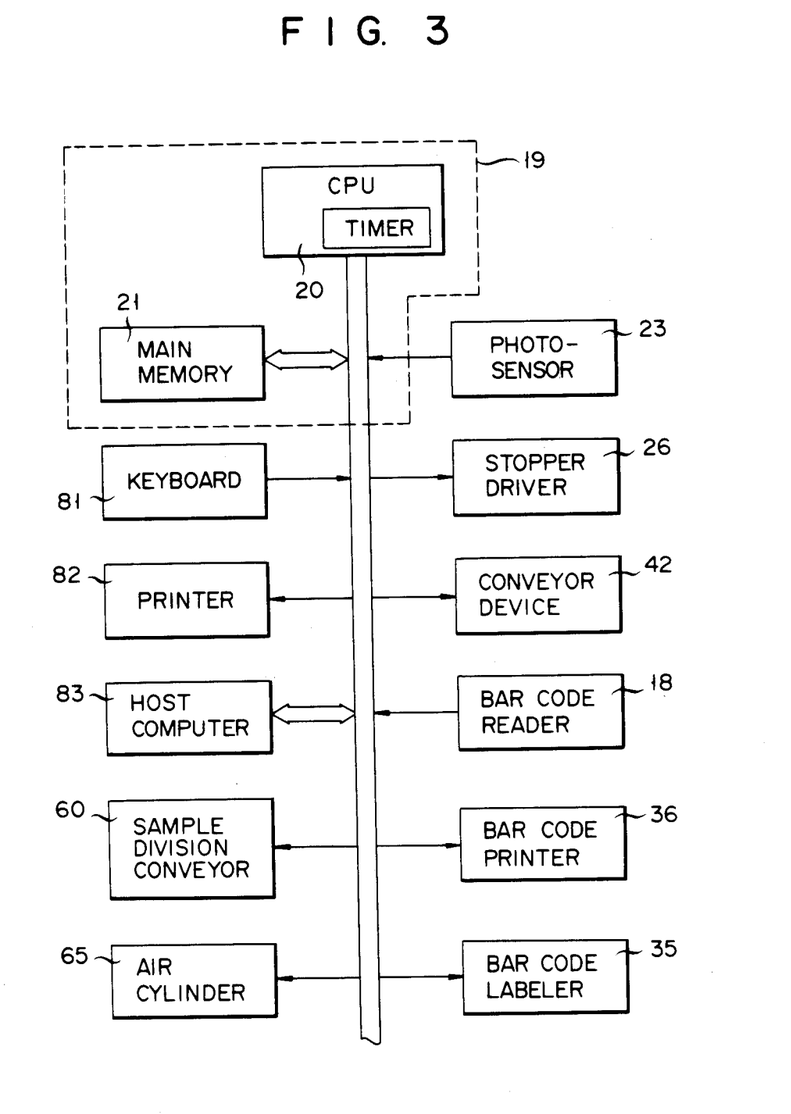
FIG. 3 is a block diagram of the control section of the apparatus.

Referring back to FIG. 1, sensors 23a and 23b, and stoppers 24a and 24b are provided besides path 11. Holders 14a to 14o, and thus tubes 12a to 12o, are transported forward in path 11 from bar code reader 18. Stoppers 24b and 24a are actuated, stopping these tubes, group by group, each group consisting of five tubes. Holders 14a to 14o in path 11, group by group, and first pass sensor 23b and then pass sensor 23a. More specifically, holders 14a to 14e holding tubes 12a to 12e of the first group are stopped by stopper 24a in the position where the blood samples will be sucked from tubes 12a to 12e. (Hereinafter, this positions will be referred to as "sample suction position.") At this time, holders 14f to 14j holding tubes 12f to 12j of the second group are stopped by stopper 24b in a first waiting position in path 11, and holders 14k to 14o holding tubes 12k to 12o of the third group are about to pass bar code reader 18. Sensors 23a and 23b, which are photosensors, receive light beams emitted from two lamps provided on the other side of path 11 and opposing them, and convert these beams into electric signals, which will be supplied to CPU 20 (FIG. 3). In FIG. 3, sensors 23a and 23b are generally indicated at numeral 23.

When the first holder 14a passes sensor 23b, CPU 20 drives stopper driver (FIG. 3), whereby stopper 24a operates, thus stopping holder 14a in the sample suction position. At the same time, the counter (not shown) provided within CPU 20 counts one. This counter outputs a signal and is reset every time its count value reaches five. As the following four holders 14a, 14c, 14d and 14e pass sensor 23b, the counter reaches the count of five. The counter thereupon outputs a signal, which is supplied to stopper driver 26. In response to this signal stopper driver 26 drives stopper 24b, whereby holders 14a to 14e, and thus tubes 12a to 12e of the first group, are stopped in the first waiting position.

In the meantime, as is shown in FIG. 1, holders 33a to 33j holding empty test tubes 32a to 32j are transported in path 31 in the direction of arrow II. Stopper 34a stops holders 33a to 33e, and thus tubes 32a to 32e, in a sample-distributing position, and stopper 34b stops holders 33f to 33j at a second waiting position. At this time, holder 33j holding empty tube 32j, is located beside a bar code labeler 35. Labeler 35 is provided to stick a label to every test tube held beside it. On the label, a bar code has been printed by bar code printer 36 provided upstream of labeler 35 with respect to path 31. Sensor 23c is provided beside path 31, downstream of stopper 34b.

Two parallel rails 38 are provided above the parallel portions of paths 11 and 31. Arm 39 is movably mounted on rails 38. Sample distributor 40 is mounted on this arm 39. The structure of sample distributor 40 will later be described in detail.

Holders 32a to 32j holding tubes 32a to 32j, respectively, are transported from path 31 and distributed to tube-dividing lane 41 after the blood samples contained in tubes 12a to 12e have been distributed among tubes 32a to 32j as will be explained later. Connected to tube-dividing lane 41 are seven lanes A to G. Lane 41 and A to G, will later be described in detail.

Path 11, holders 14a to 14o, and stoppers 24a and 24 will now be described in detail with reference to FIGS. 4 to 12.

Figure 4:
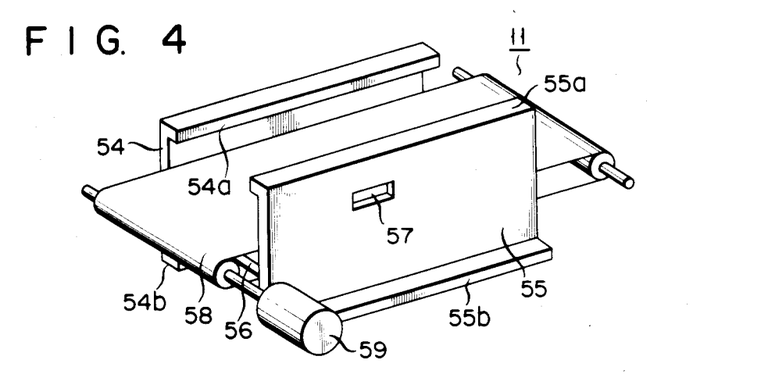
FIG. 4 is a perspective view of a tube-conveying mechanism.
Figure 5:
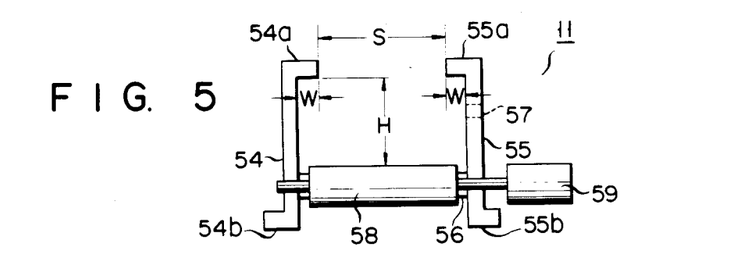
FIG. 5 is a cross-sectional view of the tube-conveying mechanism.

As is shown in FIGS. 4 and 5, path 11 comprises conveyor belt 42, and two parallel, opposing side walls 54 and 55 made of metal plates and spaced apart for a predetermined distance, and one plate 56 connecting the lower ends of side walls 54 and 55. Guide edges 54a and 55a extend from the upper ends of side walls 54 and 55, respectively, in the horizontal direction toward each other. Support legs 54b and 55b extend from the lower ends of said walls 54 and 55, respectively, in the horizontal direction, away from each other. Holes 57 are cut in side walls 54 and 55. In these holes, devices such as stopper 24a and 24b and position detectors (e.g., photosensors) for detecting holders 14a to 14o, and stoppers 24a and 24b for stopping holders 14a to 14o. Belt conveyor 42 comprises belt 58 wrapped around plate 56 connecting side walls 54. Belt 58 is driven by drive source 59 such as electric motor.

Width W of guide edges 54a and 55a, and distance S between edges 54a and 55a, and distance H between the edges 54a and 5a and upper surface of belt conveyor 58 are determined in accordance with the size and shape of holders 14a to 14o.

Figure 7:
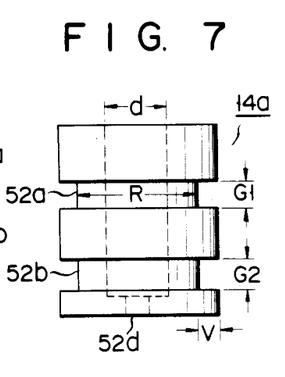
Figure 8:
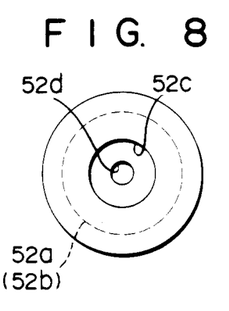

Holders 14a to 14o will now be described with reference to FIGS. 6 to 8. As is shown in these figures, each of holders 14a to 14o has two annular grooves 52a and 52b cut in the circumference, and a hole 52c extending in its axial direction. Hole 52c is provided to accommodate test tube 8. The bottom of hole 52c has a small hole 52d. Width G1 of annular groove 52a is slightly greater than the thickness of guide edges 54a and 55a. Diameter R of grooved portions of member 52 is a little smaller than distance S between guide edges 54a and 55b. Width G2 of annular groove 52b is slightly greater than the diameter of stopper pin 50a of stopper 24a, which will later be descried in detail. Diameter d of hole 52c for accommodating test tube 12a is slightly smaller than the that of test tube 12a. The diameter of hole 52d is far smaller than that of test tube 12a. Depth V of annular grooves 52a and 52b is determined by the retreated position of stopper pin 50a. Annular groove 52b can be a little deeper than annular groove 52a.

Figure 9:
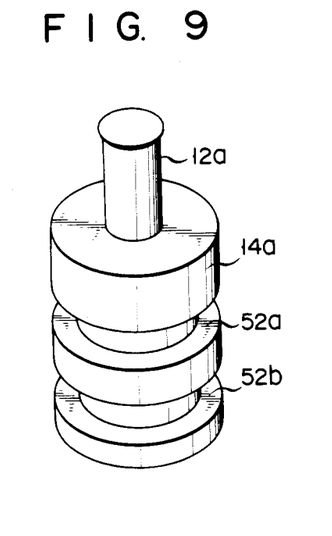
Figure 10:
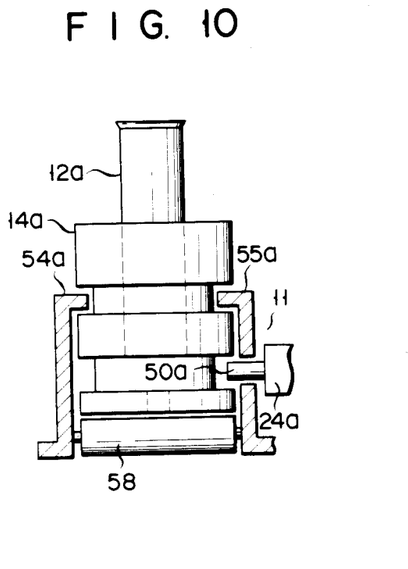
Figure 11:
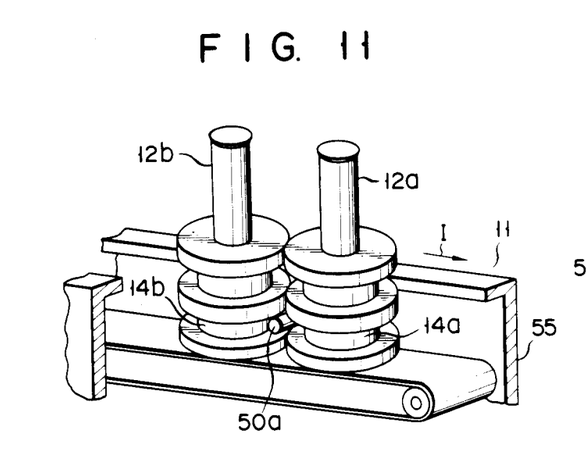
Figure 12:
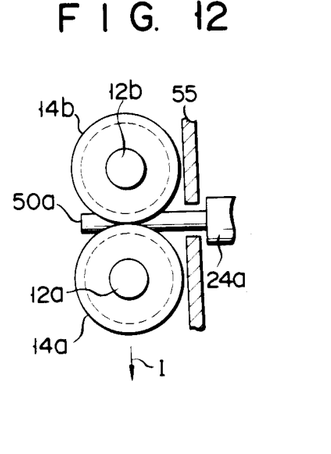

Referring to FIGS. 9 to 12, it will be explained how test tube 12a inserted in hole 52c of holder 14a is transported forward in path 11. Holder 14a holding tube 12a, as is shown in FIG. 9, is set into path 11 as is illustrated in FIG. 10. At this time, stopper 24a provided for controlling the movement of holders 14a to 14o is in its retreated position, and stopper pin 50a is completely retreated. As belt 58 is driven, holder 14a is therefore moved forward, being guided by guide edges 54a and 55a of path 11. Since guide edges 54a and 55a are inserted in annular groove 52a of holder 14a, holder 14a is stably transported, without the possibility of tipping over. When stopper 24a is actuated by CPU 20 while holder 14a to 14o are sequentially transported in path 11, stopper pin 50a thrusts into the gap between annular grooves 52a of holders 14a and 14b, as is shown in FIGS. 11 and 12. Holder 14b, located upstream of stopper pin 50a, is thus stopped. Because of annular grooves 52a, stopper pin 50a can thrust into the gap between annular grooves 52a of holders 14a and 14b, without separating holders 14a and 14b, even if two adjacent holders 14a and 14b contact each other.

Figure 13:
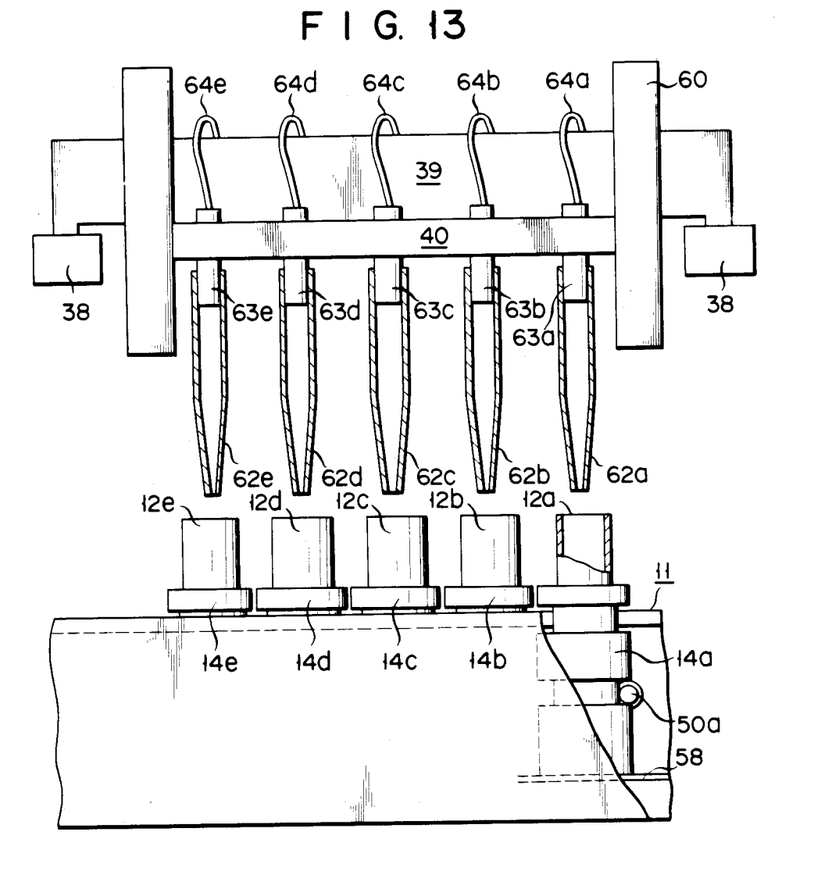
FIG. 13 schematically shows the sample distributor used in the apparatus.

With reference to FIG. 13, sample distributor 40 will be described in greater detail. When stopper 24a, which is located in the sample suction position, is driven by CPU 20, stopper pin 50a thrusts forward, whereby holders 14a to 14e, and thus test tubes 12a to 12e held in these holders, are stopped in the first sample-distributing position. When holder 14e passes sensor 23b, the counter provided in CPU 20 reaches the value of five and outputs a signal. This signal is supplied from CPU 20 to conveyor 60. In response to this signal, conveyor 60 moves arm 39 on parallel rails 38 until arm 39 reaches sensor 23d located in the sample suction position. Upon detecting arm 39, sensor 23d outputs a signal, which causes the driver to stop arm 39. As a result, sample-distributing nozzles 62a to 62e suspended from sample distributor 40 coupled to arm 39 has their lower ends located right above test tubes 12a to 12e, respectively.

Nozzles 62a to 62e is connected to pipes 63a to 63e held in vertical holes cut in sample distributor 40. Pipes 63a to 63e are connected to air cylinder 65 provided within arm 39, by flexible tubes 64a to 64e.

When sample distributor 40 reaches the sample suction position, CPU 20 causes conveyor 60 to lower arm 39 until the lower ends of nozzles 62a to 62e enter test tubes 12a to 12e and dip in blood sampled contained in tubes 12a to 12e. Then, CPU 20 gives a command to air cylinder 65. In response to the command, cylinder 65 makes nozzles 62a to 62e suck up predetermined quantities of blood samples, which have been determined by the data read by bar code reader 18.

Thereafter, CPU 20 gives another command to conveyor 60. In response to this command signal, conveyor 60 lifts arm 39, whereby nozzles 62a to 62e are pulled from test tubes 12a to 12e. Then, CPU 20 gives a command to conveyor 60, and conveyor 60 moves sample distributor 40 on rails 38 in the horizontal direction to the sample-distribution position. Sensor 23e is provided in sample-distribution position. When arm 39 reaches this position, sensor 23e detects arm 39 and produces a signal, which is supplied to conveyor 60. Upon receipt of this signal, conveyor 60 stops. As a result, the lower ends of nozzles 62a to 62e are located right above tubes 32a to 32e already brought to the sample-distributing position.

Assume that the five blood samples contained in test tubes 12a to 12e will be distributed among test tubes 32a to 32j, that is, each of these samples will be distributed among two tubes. In this case, CPU 20 outputs a signal to air cylinder 65. In response to this signal, cylinder 65 operates, thereby supplying blood samples from nozzles 62a to 62e into test tubes 32a to 32e in an equal, small quantity determined by the data read by bar code reader 18 and representing the item of analysis. The quantity of every blood sample can easily be controlled by changing the distance the air cylinder is moved. After the five blood samples have been distributed among tubes 32a to 32e, stopper pin 50a of stopper 34a is pulled out of path 31 under the control of CPU 20. Hence, holders 33a to 33e, holding tubes 32a to 32e now containing said quantities of the blood samples, are moved in path 31 to tube-dividing lane 41.

When holders 33a to 33e are transported to lane 41, stopper pin 50a of stopper 34b is pulled out of path 31 under the control of CPU 20. Holders 33f to 33j holding test tubes 32f to 32j thereby move forward in path 31 from the waiting position. When holder 33f passes detector 23c, detector 23c outputs a signal, which is supplied to CPU 20. In response to this signal, CPU operates stopper driver 26, whereby stopper pin 50a of stopper 34a thrusts into path 31. As a result, holders 33f to 33j are stopped in the sample-distributing position. Then, CPU 20 outputs a signal to air cylinder 65. In response to this signal, cylinder 65 operates, whereby the blood samples, which have been sucked from test tubes 12a to 12f, are supplied from nozzles 62a to 62e into test tubes 32f to 32j in an equal, small quantity determined by the data read by bar code reader 18 and representing the item of analysis. After the five blood samples have been distributed among tubes 32f to 32j, stopper pin 50a of stopper 34a is retreated from path 31 under the control of CPU 20. Hence, holders 33f to 33j, holding tubes 32f to 32j now containing said quantities of the blood samples, are moved in path 31 to tube-dividing lane 41. As a result, each blood sample is distributed among two test tubes.

Figure 14:
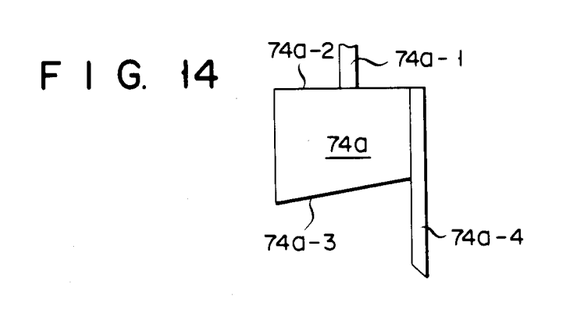
FIG. 14 schematically shows the member for dividing the tube holders into groups.

When sensor 23f, which is provided at the entrance to lane 41, detects holder 33a holding tube 32a, CPU 20 determines, from the data read by bar code reader 18, to which sorting lane, lane A, B, C, D, F or G, test tube 32a should be transported. In accordance with the decision it has made, CPU 20 controls stopper driver 26, whereby driver 26 actuates one of sorting gates 74a to 74f. Sorting gates 74a to 74f are of the same structure. As is shown in FIG. 14, each sorting gate, e.g., gate 42a, comprises drive shaft 74a-1 coupled at one end to a cylinder (not shown), plate 74a-2 secured to one end of shaft 74a-1, and strip 74a-4 extending parallel to shaft 74a-1 and connected to one side of plate 74a-2. Plate 74a-2 has slanted side 74a-3, and its side connected to strip 74a-4 is shorter than the opposing side.

With reference to FIGS. 15 to 19, it will be explained how test tubes 32a and 32b, both containing blood samples, are transported in tube-dividing lane 41 and then distributed to, for example, lane B and lane C, respectively.

Figure 15:
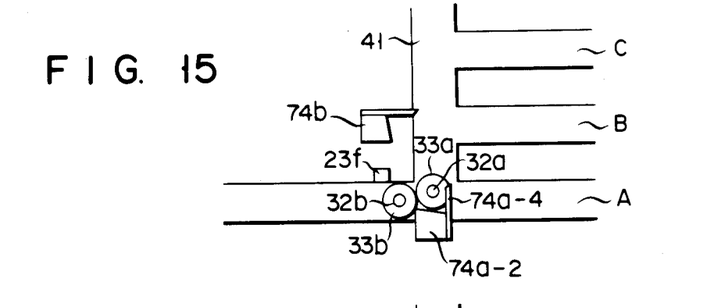
FIGS. 15 to 19 are diagrams explaining how the holders holding test tubes containing distributed quantities of the liquid sample are divided into groups.
Figure 16:
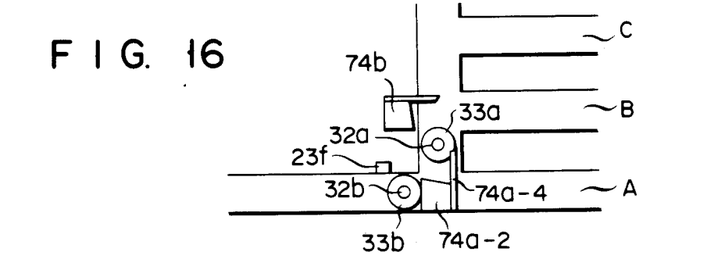

When the first holder 33a holding test tube 32a passes sensor 23f as is shown in FIG. 15, CPU 20 drives sorting gate 74a, thereby transporting test tube 32a into tube-dividing lane 41. As a result, the strip 74a-4 of gate 74a closes the entrance to lane A. Test tube 32a is therefore transported to the entrance of next lane B. Holder 33a is pushed into the corner defined by the slanted side 74a-3 and strip 74a-4 of gate 74a, and is smoothly moved toward lane B.

At this time, the second holder 33b holding second test tube 32b is stopped by plate 74a-2 of sorting gate 74a in front of lane A. Sorting gate 74a retreats and then moves forward, whereby both first and second tubes 32a and 32b are transported to the entrance to lane B.

Figure 17:
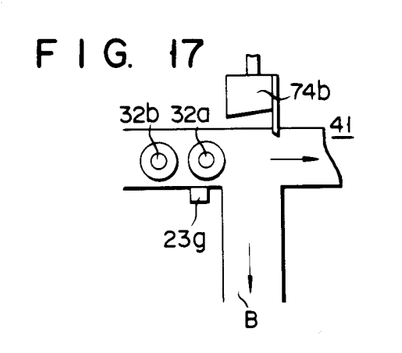
Figure 18:
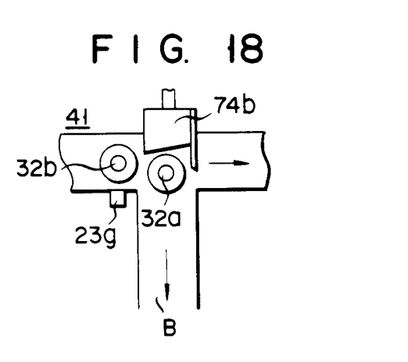
Figure 19:
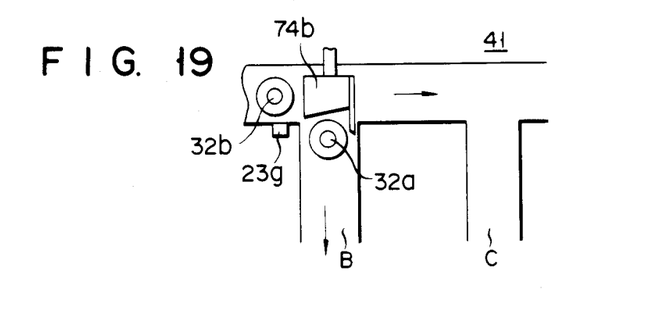

When first holder 33a passes sensor 23g as is shown in FIG. 17, CPU 20 drives sorting gate 74b, thereby transporting test tube 32a into sorting lane B as is shown in FIG. 19. At this time, second holder 33b remains stopped by sorting gate 74b in front of the entrance to lane A. When sorting gate 74b retreats, test tube 32b is transported toward next lane C.

Figure 6:
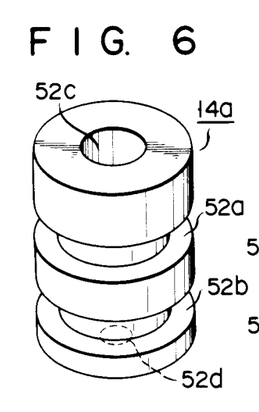
FIGS. 6 to 12 show tube holders and test tubes held by these holders.
Figure 20:
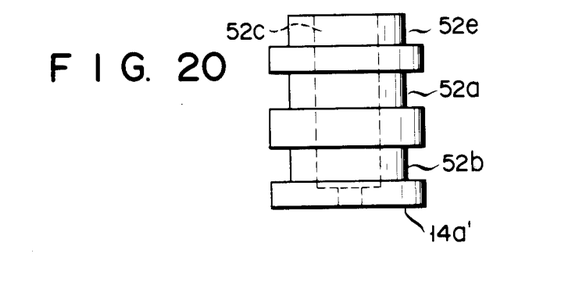
FIG. 20 is a side view of a tube holder of another type, which can be used in the invention.

As is shown in FIG. 6, holders 14a-14o has two annular grooves 52a and 52b. Holders 14a to 14o can be replaced by holders 14a', which, as is shown in FIG. 20, have three annular grooves 52a, 52b and 52d cut in the periphery. Sensors can be positioned at the level of third annular groove 52d cut in the upper portion of each holder 14', thereby to detect the presence or absence thereof.

Figure 21:
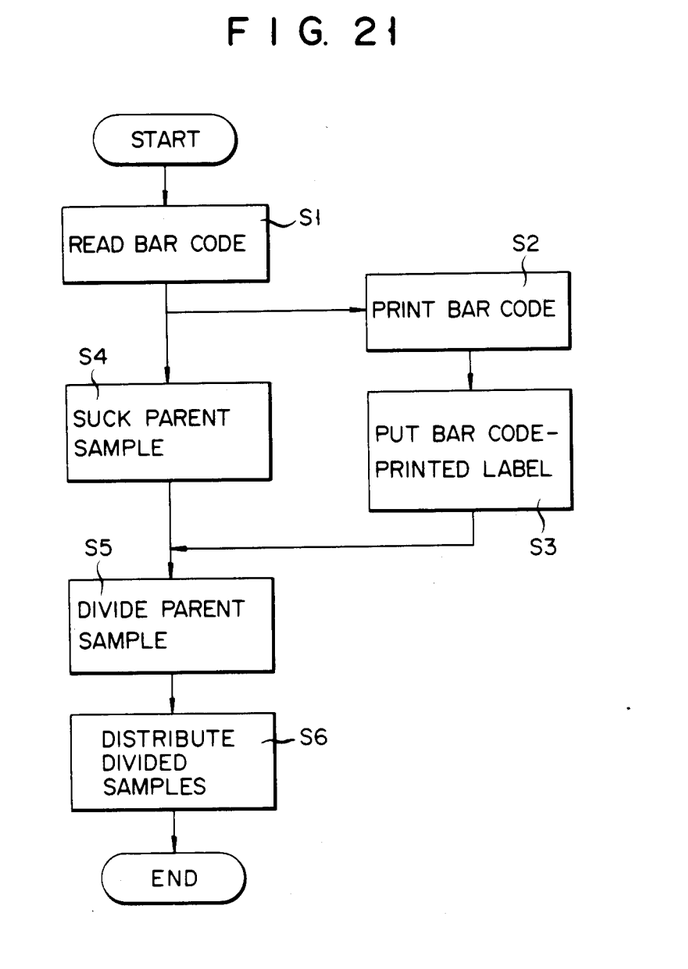
FIG. 21 is a flow chart illustrating the operation of the liquid-distributing apparatus.

Now, the operation of the liquid-distributing apparatus shown in FIGS. 1 and 3 will be explained with reference to the flow chart of FIG. 21. First, in step S1, an operator pushes the start button of keyboard 81, and bar code reader 18 reads the bar codes from test tubes 12a to 12o as these tubes pass reader 18 one after another. The data representing these bar codes is stored into main memory 21. Then, in step S2, bar code printer 36 prints the bar codes represented by this data on bland labels. In step S3, the bar code labels are sticked to test tubes 32a to 32j. In the next step, step S4, air cylinder 65 sucks quantities of the blood samples from test tubes 12a to 12e as these tubes transported to sample distributor 40. In step S5, these quantities of the blood samples are distributed, first among test tubes 32a to 32e and then among test tubes 32f to 32j. In step S6, tubes 32a to 32j are moved to tube-dividing lane 41, and are then sorted into lanes A to B.

Test tubes 32a to 32j, containing the distributed quantities of the blood samples, are removed from lanes A to G, and are further transported to different analysis devices. If necessary, printer 82 (FIG. 3) can print the data about any distributed blood sample, which has been read from main memory 21. The information about the blood samples, such as the blood sample numbers, the lane numbers, and the distributed quantities of the samples, can be input by operating keyboard 81, or can be supplied from a host computer (not shown) to CPU 20.

According to the invention, a quantity-measuring device (not shown) can be provided beside path 11 and downstream of bar code reader 18. This device is designed to measure the distance between it and the surface level of the blood sample in each test tube, thus determining whether or not the tube contains a sufficient amount of a sample blood. More precisely, it emits a light beam or an ultrasonic beam to the surface of the blood sample in the tube. The distance between the device and the surface level of the blood sample is measured from the time which has elapsed until the beam reaches to the device from the surface of blood sample. Sorting gate 80, identical to gates 74a to 74f in structure, is provided between the quantity-measuring device and stopper 24b as is shown in FIG. 1. When the quantity of the sample in the tube is insufficient, sorting gate 80 is operated to remove the test tube from path 11 into discharge path 11a.

In the embodiment of FIG. 1, any test tube containing a blood sample, that is set in front of bar code reader 18, has already been opened. The tube can be opened by an automatic test tube plug extraction apparatus as is disclosed in PCT Application No. PCT/JP87/00199 filed on Mar. 31, 1987 by the same applicant as the present application.

What is claimed is:

1. A liquid-distributing apparatus comprising:
a sample-transporting means including holders for holding containers, a conveyor for conveying the holders, and guide means for guiding the holders to a first position where liquid samples will be sucked from some of the containers held by some of the holders, each holder being a hollow cylinder having at least two annular grooves cut in its outer periphery, said guide means having guide edges insertable in the first of said two annular grooves of the holder;
data-reading means for reading, from each of the containers containing a liquid sample, data showing items for which the sample will be analyzed and data showing the identity of the sample;
means for transporting the holders holding empty containers in the same number as the items of analysis to a second position where each liquid sample will be distributed among the empty containers;
means for distributing the liquid sample in small quantities from each of the containers located in said first position, among the containers located in said second position, in accordance with the data read by the data-reading means; and
means for dividing the containers containing the small quantities of the liquid samples into groups in accordance with the data read by the data-reading means.

2. The apparatus according to claim 1, wherein said means for dividing the containers has a main plate projecting into said sample-transporting path, and an auxiliary plate connected to one side of the main plate, said main plate and said auxiliary plate cooperating to push one container, while the main plate is stopping the next container.

3. The apparatus according to claim 1, wherein said means for transporting the holders holding empty containers includes a stopper having a stopper pin capable of thrusting into the gap between the second of said two annular grooves of each of two adjustment holders, the second groove of each holder being free from said guide edges of said guide means.

4. The apparatus according to claim 3, wherein said conveyor is continuously driven, and any container can be stopped at a predetermined position on said conveyor when said stopper pin thrusts into the gap between the second of said two annular grooves of the holder holding this container and the second of said two annular grooves of the holder holding the preceding container.

5. The apparatus according to claim 1, wherein said means for distributing the liquid samples has disposable nozzles which are inserted into said containers.

6. The apparatus according to claim 1, wherein said data is represented by a bar code.

* * * * *